US005656255A

United States Patent [19]
Jones

[11] Patent Number: 5,656,255
[45] Date of Patent: Aug. 12, 1997

[54] COMPOSITION TO HELP STOP SMOKING

[75] Inventor: Richard L. Jones, Edmonton, Canada

[73] Assignee: Pharmacia & Upjohn AB, Sweden

[21] Appl. No.: 256,312

[22] PCT Filed: Jan. 4, 1993

[86] PCT No.: PCT/CA93/00003

§ 371 Date: Sep. 29, 1994

§ 102(e) Date: Sep. 29, 1994

[87] PCT Pub. No.: WO93/12764

PCT Pub. Date: Jul. 8, 1993

[30] Foreign Application Priority Data

Jan. 3, 1992 [GB] United Kingdom ............. 9200047

[51] Int. Cl.$^6$ ............................................. A61K 9/12
[52] U.S. Cl. ....................................... 424/43; 424/434
[58] Field of Search ................................ 424/434, 43

[56] References Cited

U.S. PATENT DOCUMENTS

| | | | |
|---|---|---|---|
| 4,579,858 | 4/1986 | Fernö et al. | 514/343 |
| 4,715,387 | 12/1987 | Rose et al. | 131/270 |
| 4,920,989 | 5/1990 | Rose et al. | 131/270 |
| 4,934,358 | 6/1990 | Nilsson et al. | 128/200.23 |
| 4,945,929 | 8/1990 | Egilmex | 131/273 |
| 4,953,572 | 9/1990 | Rose et al. | 131/270 |

FOREIGN PATENT DOCUMENTS

| | | |
|---|---|---|
| 3241437 A1 | 5/1984 | Germany . |
| 3241437 | 5/1984 | Germany . |
| 2030862 | 4/1980 | United Kingdom . |
| 2133691 | 8/1984 | United Kingdom . |

OTHER PUBLICATIONS

Nasal nicotine solution: a potential aid to giving up smoking?, Russell et al., (1983), *British Medical Journal*, v. 286, pp. 683–684.

Nasal Nicotine Solution as an Aid to Cigarette Withdrawal: a pilot clinical trial, Jarvis et al., (1987), *British Journal of Addiction*, v. 82, pp. 983–988.

*Transdermal Nicotine as a Strategy for Nicotine Replacement*, Rose, J., (1986), in "Pharmacologic Treatment of Tobacco Dependence", Ed. J.K. Ockene, at pp. 158–166.

An aerosol spray alternative to cigarette smoking in the study of the behavioral and physiological effects of nicotine, Perkins et al., (1986) *Behavior Research Methods, Instruments & Computers*, v. 18, pp. 420–426.

Chronic and acute tolerance to the heart rate effects of nicotine, Perkins et al., (1989), *Psychopharmacology*, v. 97, pp. 529–534.

Research Disclosure 239015, Derwent, Feb. 20, 1984.

*Primary Examiner*—Jyothsan Venkat
*Attorney, Agent, or Firm*—Dinsmore & Shohl LLP

[57] ABSTRACT

A composition for administration to the nasal mucosa of a subject comprises a solution of nicotine or a pharmaceutically acceptable salt thereof in a pharmaceutically acceptable solvent. The composition has a nicotine concentration in the range of about 10 to about 40 mg/ml and contains a suitable agent to produce a viscosity in the range of about 1 to about 30 centipoise. The composition assists in reduction of the desire of the subject to smoke tobacco or provides a substitute for tobacco smoking.

22 Claims, 1 Drawing Sheet

COMPOSITION TO HELP STOP SMOKING

This application is a 371 of PCT/CA93/00003 filed Jan. 4, 1993.

This invention relates to compositions and methods useful for subjects who wish to reduce tobacco smoking or to find a socially acceptable substitute.

BACKGROUND OF THE INVENTION

Because of the reported harmful effects of tobacco smoking and also due to the current social attitudes to smoking, resulting in ever-increasing smoke-free public areas, there is great pressure on tobacco smokers to stop smoking or to find a more socially acceptable alternative.

For those who are unable to give up smoking completely, various forms of nicotine-replacement therapy have been suggested.

Nicotine-containing chewing gum is available commercially and has provided a satisfactory substitute for tobacco-smoking for some people. For many people, nicotine gum does not alleviate the craving for tobacco, due to the gradually achieved and low blood nicotine levels produced. Many people also experience unpleasant side effects, such as nausea and indigestion (Jarvis et al., British Medical Journal, Vol. 285, p. 537 (1982); Schneider, Comprehensive Therapy, Vol. 13, p. 32 (1987)).

Nicotine-containing nose drops have been reported (Russel et al., British Medical Journal, Vol. 286, p. 683 (1983); Jarvis et al., Brit. J. of Addiction, Vol. 82, p. 983 (1987)). Nose drops, however, are difficult to administer and are not convenient for use at work or in other public situations. There may also be local nasal irritation with use of nicotine nose drops. The difficulty in administration also results in unpredictability of the dose of nicotine administered.

The use of skin patches for transdermal administration of nicotine has been reported (Rose, in Pharmacologic Treatment of Tobacco Dependence, (1986) pp. 158–166, Harvard Univ. Press). Nicotine-containing skin patches can cause local irritation and the absorption of nicotine is slow and affected by cutaneous blood flow.

U.S. Pat. Nos. 4,920,989 and 4,953,572 disclose the use of an inhaled nicotine aerosol, sometimes in conjunction with nicotine skin patches, as a means of reducing tobacco smoking. When skin patches were used, transdermal absorption of nicotine gave blood nicotine levels comparable to those achieved by tobacco smoking. The use of the nicotine aerosol alone delivered substantially less nicotine to the blood than is seen while smoking tobacco but did provide sensations of irritation in the airways of the user, thus mimicking sensations associated with tobacco smoking.

In order to ensure that the droplets of nicotine solution would be carried into the respiratory airways on inhalation through the mouth in imitation of smoking, rather than being deposited in the oral cavity, the aerosol droplet size employed was 10 microns or less.

Although a certain degree of airway irritation is desired to mimic smoking, this cannot be readily controlled and the irritation may be pronounced, making the use of a nicotine aerosol undesirable.

Perkins et al. (Behavior, Research Methods, Instruments and Computers (1986), vol. 18, p.420 and Psychopharm. (1989), vol. 97, p. 529) reported use of a nicotine aerosol spray as a means of administering nicotine to a test subject in controllable amounts in order to study the physiological effects of nicotine. Under their test conditions, they were able to employ a dilute solution of nicotine administered in several doses to deliver 1.8 ml. over a 5 minute period to resting subjects and did not investigate a practical nicotine preparation for everyday use, such as is required for anti-smoking treatment or as a substitute for tobacco smoking.

U.S. Pat. No. 4,579,858 discloses a nicotine-containing preparation of high viscosity which is administered to the nose as a viscous plug. The surface area of such a plug which is in contact with the nasal mucosa is limited and this is reflected in the relatively low blood nicotine levels achieved by this method of nicotine administration.

There remains a need for a nicotine preparation suitable as a substitute for tobacco smoking, which can be conveniently used in public, as the subject goes about his or her normal activities over an extended period of time.

SUMMARY OF INVENTION

A composition for nasal administration is provided to assist in reduction of the desire of a subject to smoke tobacco or to provide a substitute for tobacco smoking, the composition comprising a solution of nicotine or a pharmaceutically acceptable salt thereof in a pharmaceutically acceptable solvent, the composition having a pH in the range of about 5 to about 6.5, a nicotine concentration in the range of about 10 to about 40 mg/ml and containing a suitable agent to produce a viscosity in the range of about 1 to about 99 centipoise.

SUMMARY OF THE DRAWINGS

The invention, as exemplified by preferred embodiments, is described with reference to the drawings in which.

DETAILED DESCRIPTION OF THE INVENTION

Figure 1:
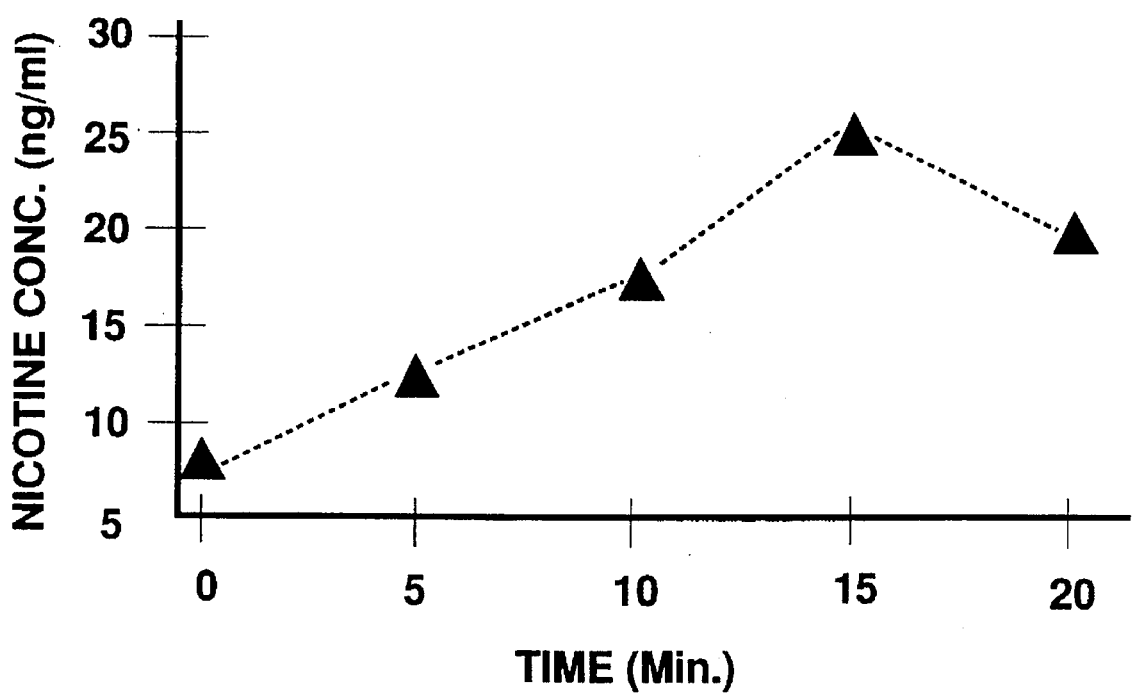
FIGURE 1 shows the blood nicotine level of a subject at various time intervals after administration of the nicotine-containing composition of the invention.

The present invention provides a convenient, inexpensive and effective alternative to tobacco smoking, by administration of an effective dose of nicotine by nasal spray to a subject.

Nicotine-containing compositions and nasal sprays suitable for nasal administration are also provided.

The smoking alternative provided by the present invention may be used to assist those attempting to stop tobacco smoking or may be used indefinitely as a substitute for tobacco smoking which avoids both the undesired side effects of tobacco smoking on other people in the vicinity of the smoker and also the deleterious effects on the smoker of other substances such as carcinogens and carbon monoxide in tobacco smoke. The nicotine-containing compositions and sprays of the invention may be used without interference with the user's productive work or other normal activities.

When a nicotine-containing solution is applied to the nasal mucosa, nicotine can be absorbed directly into the bloodstream. If a smoking substitute is to be provided by this means, sufficient nicotine must be applied and absorbed to give a rapid increase in blood nicotine comparable to that achieved by tobacco smoking if the craving to smoke is to be eliminated. Previously available smoking substitutes often fail in this regard due to a too small or too delayed increase in blood nicotine level.

It is desirable that nasal administration of nicotine provides a sufficient dose of nicotine to a sufficiently large area of the nasal mucosa to give the desired rapid increase in blood nicotine level without providing a local nicotine concentration so high that it causes mucosal irritation and without requiring the delivery of such a large volume of nicotine-containing composition that a portion of the administered dose runs from the nose, causing annoyance and inconvenience to the user.

In accordance with the present invention, nicotine or a pharmaceutically acceptable nicotine salt is dissolved in a pharmaceutically acceptable solvent, such as phosphate-buffered saline, and is adjusted to a pH in the range of about 5 to about 6.5, for optimal absorption through the nasal mucosa. A pH of about 5.8 is preferred.

Pharmaceutically acceptable nicotine salts are known to those skilled in the art and include nicotine tartrate and nicotine hydrogen tartrate.

Other suitable pharmaceutically acceptable buffering agents will be known to those skilled in the art.

In order to improve retention of the nicotine-containing composition of the invention in the nose, a suitable agent is added to produce a viscosity in the range of about 1 to about 99 centipoise. A viscosity in the range of about 10 to about 20 centipoise is preferred.

As will be known to those skilled in the art, a variety of agents may be used to produce the desired viscosity, including cellulose, substituted celluloses such as carboxymethyl cellulose and methyl cellulose, gum arabic and polyethylene glycol. The desired viscosity may also be produced by use of an oil emulsion, the oil phase being any suitable nasally-acceptable oil including, for example, lanolin or beeswax. Any viscosity producing agent used must, of course, be pharmaceutically acceptable and well tolerated by the nasal mucosa.

The nicotine-containing composition of the present invention is applied to the nose as a spray of droplet size selected to favour deposition of the droplets in the nose and minimise inhalation of the nicotine composition into the airways beyond the nose.

Studies by Yu et al (J. Pharmaceut. Sci., Vol. 73, p. 344 (1984)) have shown that droplet size of a spray delivered into the nose or inhaled through the mouth influences the location of droplet deposition. These authors showed that, during inhalation, droplets of 2 to 6 microns largely reach the terminal bronchi and alveoli, whereas a majority of droplets greater than 10 microns is required to localise delivery in the nose.

The nicotine-containing composition of the invention may be applied to the nose by any suitable atomiser or spray device which produces a spray of droplet size greater than about 10 microns. For example, conventional venturi-type atomisers such as are used for nasal decongestants or metered dose spray devices such as are used for nasal steroid application may be employed. These devices produce 98% of droplets greater than 16 microns and a majority of droplets of approximately 100 to 200 microns. As will be understood by those skilled in the art, the viscosity of the composition of the invention should be optimised for the type of spray device employed. For example, it has been found by the inventors that when a venturi-type atomiser is used, the nicotine composition should have a viscosity of not more than about 10 centipoise. When a metered dose spray device is used, a composition of viscosity up to about 30 centipoise may be used with good droplet production, with increasing viscosities above that tending to produce a stream of liquid rather than an aerosol. A suitable composition viscosity for a particular type of spray device may be readily determined by those skilled in the art.

When then nasal spray of the invention is used, nicotine is not drawn into the user's airways beyond the nose, thus avoiding respiratory irritation and allowing the use of higher nicotine concentrations, permitting blood nicotine levels to be boosted to those comparable with smoking without concomitant irritation.

As will be understood by those skilled in the art, the nicotine concentration in the composition of the invention and the volume of composition delivered to the nose may be varied to provide a desired nicotine dose to a subject. The volume delivered should be selected to as to be well retained in the nose, without running out. The nicotine concentration should not be so high as to produce unacceptable local irritation when sprayed in the required amount.

The inventors have found that the composition of the invention can be applied in a volume of about 0.03 to about 0.08 ml. per nostril with good retention of the composition in the nose. A nicotine concentration in the range of about 10 to about 40 mg/ml is well tolerated by the nasal mucosa when applied in accordance with the present invention.

In order to approximate the dose of nicotine delivered to the blood by smoking one cigarette, is, approximately 1 mg (Russell et al., above), about 2 mg nicotine should be delivered to the nose. If, for example, an atomiser delivering about 0.03 ml. nicotine composition per squeeze is employed, and the composition has a concentration of 20 mg/ml nicotine, one squeeze delivers 0.06 mg nicotine and three applications will deliver approximately 2 mg nicotine.

In accordance with a preferred embodiment of the invention, a composition having a viscosity of about 10 centipoise and nicotine concentration about 20 mg/ml, dissolved in phosphate buffered saline at a pH of about 5.8 is employed. The composition is delivered to the nose by a spray device which delivers about 0.03 ml. of the composition per activation of the device in the form of a spray having droplets of at least 10 microns diameter.

The nicotine composition of the invention may also optionally contain one or more of a flavouring agent such as menthol, and a preserving agent such as benzoic acid or an antioxidant such as ascorbic acid. Suitable flavourings and preservatives acceptable in foods and pharmaceuticals will be known to those skilled in the art, as will suitable concentrations of these agents.

Use of nicotine-containing compositions of the invention applied as a nasal spray in accordance with the invention has been found to be well tolerated by human subjects, with minimal side effects in the form of a mild and temporary runny nose.

Use of the nicotine-containing nasal spray of the invention has been found to permit a smoker to function efficiently in a non-smoking work environment for at least three years without withdrawal symptoms or tobacco cravings.

The following examples are merely illustrative of the invention and the invention is not necessarily limited thereto.

EXAMPLE 1

Nicotine (98–100% free base, catalogue #3876, Sigma Chemical Co., St Louis, Mo.) was dissolved in phosphate buffered saline (PES: 0.175 g $Na_2HPO_4$/100 ml; 1.21 g $NaH_3PO_4$/100 ml; 0.292 g NaCl/100 ml) to give a nicotine concentration of 20 mg/ml. This solution has a pH of 5.8 and an osmolarity of 290 mosm. Carboxymethyl-cellulose was added to give a viscosity of 5 centipoise. The solution was sterilised by passing it through a 0.2 micron filter and 10 ml of the sterilised solution was placed in a conventional venturi-type atomiser.

The atomiser was used to administer 2.4 mg nicotine to the nose of a human subject over about 5 seconds, by four squeezes of the atomiser (two squeezes into each nostril). Blood samples were collected from an anticubital vein in the arm of the subject at various time intervals after nicotine administration (time zero in FIGURE 1) and blood nicotine concentrations were determined by the method of Feyerabend and Russell (J. Pharm. Pharmacol., Vol. 32, pp. 178–181 (1980)). Results are shown in FIGURE 1.

The concentrations of blood nicotine achieved were similar to those resulting from smoking of a cigarette and the peak value occurred around 15 minutes from administration, only slightly later than after cigarette smoking.

Although only preferred embodiments of the invention have been described and illustrated, the present invention is not limited to the features of these embodiments, but includes all variations and modifications within the scope of the claims.

I claim:

1. A nicotine-containing spray for administration to the nasal mucosa of a subject to assist in reduction of the desire of the subject to smoke tobacco or to provide a substitute for tobacco smoking, the spray being in the form of droplets of a size in the range of from about 10 to about 200 microns and comprising a solution of nicotine or a pharmaceutically acceptable salt thereof in a pharmaceutically acceptable solvent, the spray having a nicotine concentration in the range of about 10 to about 40 mg/ml and further comprising a viscosity agent providing the spray with a viscosity in the range of about 1 to about 30 centipoise.

2. A spray in accordance with claim 1 wherein the pharmaceutically acceptable solvent is phosphate buffered saline.

3. A spray in accordance with claim 1 wherein the viscosity agent is cellulose or a substituted cellulose.

4. A spray in accordance with claim 1 wherein the viscosity agent is carboxymethyl cellulose.

5. A spray in accordance with claim 1 wherein the viscosity agent is a pharmaceutically acceptable oil emulsion.

6. A spray in accordance with claim 1 wherein the pH is in the range of about 5 to about 6.5

7. A spray in accordance with claim 1 wherein the pH is about 5.8 and the nicotine concentration is about 20 mg/ml, and wherein the spray contains carboxymethyl cellulose to provide the spray with a viscosity of about 5 to about 20 centipoise.

8. A nicotine containing spray in accordance with claim 1, wherein the droplets are about 100 to about 200 microns in diameter.

9. A spray in accordance with claim 1, wherein the spray is delivered from a spray device for delivering an effective dose of the spray to the nose.

10. A spray in accordance with claim 1, further comprising one or more agents selected from the group consisting of a flavouring agent, a preserving agent and an antioxidant.

11. A method of assisting in the reduction of the desire of a subject to smoke tobacco, comprising administering an effective dose of a nicotine-containing spray in accordance with any one of claims 2 to 5, 6 or 8 to the nasal mucosa of the subject.

12. A method of assisting in the reduction of the desire of a subject to smoke tobacco, comprising administering an effective dose of a nicotine-containing spray in accordance with claim 8 to the nasal mucosa of the subject.

13. A method of assisting in the reduction of the desire of a subject to smoke tobacco, comprising administering a nicotine-containing spray in accordance with claim 7 to the nasal mucosa of the subject.

14. A method of providing to a smoker a substitute for tobacco smoking, comprising administering an effective dose of a nicotine-containing spray in accordance with any one of claims 2 to 5, 6 or 7 to the nasal mucosa of the subject.

15. A method of providing to a smoker a substitute for tobacco smoking, comprising administering an effective dose of a nicotine-containing spray in accordance with claim 8 to the nasal mucosa of the subject.

16. A method of providing to a smoker a substitute for tobacco smoking, comprising administering a nicotine-containing spray in accordance with claim 7 to the nasal mucosa of the subject.

17. A method of assisting in the reduction of the desire of a subject to smoke tobacco, comprising administering an effective dose of a nicotine-containing spray in accordance with claim 1.

18. A method of assisting in the reduction of the desire of a subject to smoke tobacco, comprising administering a nicotine-containing spray in accordance with claim 1 to the nasal mucosa of the subject in an amount which delivers a nicotine dose in the range of about 1 to about 3 mg.

19. A method of providing to a smoker a substitute for tobacco smoking, comprising administering an effective dose of a nicotine-containing spray according to claim 1 to the nasal mucosa of the subject.

20. A method of providing to a smoker a substitute for tobacco smoking, comprising administering a nicotine-containing spray in accordance with claim 1 to the nasal mucosa of the subject in an amount which delivers a nicotine dose in the range of about 1 to about 3 mg.

21. A method according to claim 17, wherein the nicotine-containing spray is administered in a volume of about 0.03 to about 0.08 ml.

22. A method according to claim 19, wherein the nicotine-containing spray is administered in a volume of about 0.03 to about 0.08 ml.

* * * * *

UNITED STATES PATENT AND TRADEMARK OFFICE
CERTIFICATE OF CORRECTION

PATENT NO. : 5,656,255
DATED : August 12, 1997
INVENTOR(S) : Richard L. Jones

It is certified that error appears in the above-indentified patent and that said Letters Patent is hereby corrected as shown below:

Claim 11, column 6, line 7, change "8" to --7--.

Signed and Sealed this

Seventh Day of October, 1997

Attest:

BRUCE LEHMAN

*Attesting Officer*  *Commissioner of Patents and Trademarks*